United States Patent
Lin

(10) Patent No.: US 9,140,655 B2
(45) Date of Patent: Sep. 22, 2015

(54) MOTHER GLASS INSPECTION DEVICE AND MOTHER GLASS INSPECTION METHOD

(71) Applicant: Shenzhen China Star Optoelectronics Technology Co., Ltd., Shenzhen, Guangdong (CN)

(72) Inventor: Yungyu Lin, Shenzhen (CN)

(73) Assignee: Shenzhen China Star Optoelectronics Technology Co., Ltd., Shenzhen, Guangdong (CN)

( * ) Notice: Subject to any disclaimer, the term of this patent is extended or adjusted under 35 U.S.C. 154(b) by 98 days.

(21) Appl. No.: 13/814,749

(22) PCT Filed: Jan. 6, 2013

(86) PCT No.: PCT/CN2013/070086
§ 371 (c)(1),
(2) Date: Feb. 7, 2013

(87) PCT Pub. No.: WO2014/101310
PCT Pub. Date: Jul. 3, 2014

(65) Prior Publication Data
US 2014/0185040 A1      Jul. 3, 2014

(30) Foreign Application Priority Data

Dec. 27, 2012   (CN) .......................... 2012 1 0580384

(51) Int. Cl.
*G01N 21/00*      (2006.01)
*G01N 21/958*      (2006.01)
*G01N 21/95*      (2006.01)

(52) U.S. Cl.
CPC ...... *G01N 21/958* (2013.01); *G01N 2021/9513* (2013.01)

(58) Field of Classification Search
USPC ........... 356/237.1–237.5, 239.1, 239.2, 239.8
See application file for complete search history.

(56) References Cited

U.S. PATENT DOCUMENTS

| | | | |
|---|---|---|---|
| 3,039,349 A * | 6/1962 | Rodgers .................. | 359/601 |
| 3,857,637 A * | 12/1974 | Obenreder ............... | 356/613 |
| 4,568,835 A * | 2/1986 | Imamura et al. ......... | 250/559.41 |
| 4,966,457 A * | 10/1990 | Hayano et al. ............ | 356/239.7 |
| 5,245,403 A * | 9/1993 | Kato et al. ................ | 356/239.8 |
| 5,298,974 A * | 3/1994 | Chandley ................. | 356/613 |
| 6,166,808 A * | 12/2000 | Greve ...................... | 356/601 |
| 2002/0125449 A1* | 9/2002 | Ishiguro et al. .......... | 250/559.45 |
| 2004/0207836 A1* | 10/2004 | Chhibber et al. ......... | 356/237.4 |
| 2008/0090029 A1* | 4/2008 | Hoshino et al. .......... | 428/29 |

FOREIGN PATENT DOCUMENTS

| | | |
|---|---|---|
| CN | 1147634 A | 4/1997 |
| CN | 1354362 A | 6/2002 |

(Continued)

*Primary Examiner* — Hoa Pham
(74) *Attorney, Agent, or Firm* — Andrew C. Cheng

(57) ABSTRACT

The present invention provides a mother glass inspection device and a mother glass inspection method. The inspection device includes: a main body, a platform mounted on the main body, a light absorption layer formed on a top surface of the platform, a laser transmitter mounted on the main body and opposing the platform, and an image sensor arranged above the platform to correspond to the laser transmitter. The platform supports a piece of mother glass to be laid flat thereon. The mother glass inspection device adopts a flat-laying type platform to support a piece of mother glass and provides a light absorption layer on the platform so as to eliminate fault inspection result of the image sensor caused by light reflection by stains present on the back side of the mother glass.

7 Claims, 3 Drawing Sheets

(56) References Cited

FOREIGN PATENT DOCUMENTS

| CN | 1517697 A | 8/2004 |
| CN | 101517400 A | 8/2009 |
| CN | 201699810 U | 1/2011 |
| CN | 102141526 A | 8/2011 |
| CN | 102455303 A | 5/2012 |
| JP | 2007-196608 * | 8/2007 |

* cited by examiner

MOTHER GLASS INSPECTION DEVICE AND MOTHER GLASS INSPECTION METHOD

BACKGROUND OF THE INVENTION

1. Field of the Invention

The present invention relates to the field of liquid crystal display, and in particular to processing of a mother glass of a liquid crystal panel of a liquid crystal display device.

2. The Related Arts

Today's vigorous development of science and technology brings constantly innovated information products to suit various needs of the public. Displays of the early time are most CRT (Cathode Ray Tube) displays, which are bulky and consume a large amount of electrical power and may generate radiation that is hazard to body health for users who use the displays for a long time. Thus, for the displays that are currently available in the market, liquid crystal displays (LCDs) are gradually taking the place of the CRT displays.

The liquid crystal displays have a variety of advantages, such as thin device body, low power consumption, and being free of radiation, and is thus widely used. Most of the LCDs that are currently available in the market are backlighting LCDs, which comprise a liquid crystal panel and a backlight module. The operative principle of the liquid crystal panel is that liquid crystal molecules are interposed between two parallel glass substrates and the liquid crystal molecules are controlled to change direction by a circuit formed on the glass substrates in order to refract out light emitting from the backlight module for generating images. Since the liquid crystal panel itself does not emit light, light must be provided by the backlight module in order to normally display images. Thus, the backlight module is one of the key components of the LCDs. The backlight module can be classified in two types, namely side-edge backlight module and direct backlight module, according to the position where light gets incident. The direct backlight module comprises a light source, such as a cold cathode fluorescent lamp (CCFL) or a light-emitting diode (LED), which is arranged at the back side of the liquid crystal panel to directly provide a planar light source to the liquid crystal panel. The side-edge backlight module comprises a backlight source comprising an LED light bar that is arranged at an edge of a backplane to be located rearward of one side of the liquid crystal panel. The LED light bar emits light that enters a light guide plate (LGP) through a light incident face at one edge of the light guide plate and is projected out of a light emergence face of the light guide plate, after being reflected and diffused, to transmit through an optic film assembly thereby forming a planar light source for the liquid crystal panel In a manufacturing process of a liquid crystal display panel, processing of a piece of mother glass is involved, wherein a mother glass laser inspection device is employed to inspect the processed piece of mother glass. Referring to FIG. 1, a conventional mother glass laser inspection device adopts a pin type platform 100, whereby in inspecting the mother glass 200, stains (such as roller marks) formed on a back surface of the mother glass 200 will cause reflection of laser so that an image sensor 300 (which is a charge-coupled device) will receive the reflected light and makes erroneous identification of a particle located on a front surface of the mother glass 200. Consequently, an incorrect inspection of the mother glass 200 results. This may causes a need for reworking or disposal and as a result, production efficiency and yield are lowered down and at the same time, working hours and cost are increased.

SUMMARY OF THE INVENTION

An object of the present invention is to provide a mother glass laser inspection device, which improves the influence on inspection operation caused by a back side stain of the mother glass and avoids fault result of inspection so as to precisely identify if abnormality is present on a product to thereby prevent erroneous reworking or disposal for improving manufacturing efficiency and yield rate, shortening working hours, and lowering manufacturing cost.

Another object of the present invention is to provide a mother glass laser inspection method, which is easily operated and may avoid fault result of inspection so as to prevent erroneous reworking or disposal for improving manufacturing efficiency and yield rate, shortening working hours, and lowering manufacturing cost.

To achieve the objects, the present invention provides a mother glass inspection device, which comprises: a main body, a platform mounted on the main body, a light absorption layer formed on a top surface of the platform, a laser transmitter mounted on the main body and opposing the platform, and an image sensor arranged above the platform to correspond to the laser transmitter. The platform functions to support a piece of mother glass to be laid flat thereon.

The light absorption layer is formed by coating a light absorption material on the platform.

The laser transmitter comprises a laser head and a reflector arranged to correspond to the laser head. The reflector reflects and re-directs a beam emitting from the laser head to the platform.

The image sensor comprises a photo detector. The photo detector is electrically connected to the main body to receive light emitting from the laser head and reflected by the mother glass.

The main body comprises: an enclosure and a circuit arrangement provided inside the enclosure. The circuit arrangement comprises a power module and a processing module. The power module is electrically connected to the processing module, the image sensor, and the laser transmitter. The processing module is further electrically connected to the image sensor and the laser transmitter.

The present invention also provides a mother glass inspection device, which comprises: a main body, a platform mounted on the main body, a light absorption layer formed on a top surface of the platform, a laser transmitter mounted on the main body and opposing the platform, and an image sensor arranged above the platform to correspond to the laser transmitter, the platform being adapted to support a piece of mother glass to be laid flat thereon;

wherein the light absorption layer is formed by coating a light absorption material on the platform;

wherein the laser transmitter comprises a laser head and a reflector arranged to correspond to the laser head, the reflector reflecting and re-directing a beam emitting from the laser head to the platform;

wherein the image sensor comprises a photo detector, the photo detector being electrically connected to the main body to receive light emitting from the laser head and reflected by the mother glass; and wherein the main body comprises: an enclosure and a circuit arrangement provided inside the enclosure, the circuit arrangement comprising a power module and a processing module, the power module being electrically connected to the processing module, the image sensor, and the laser transmitter, the processing module being further electrically connected to the image sensor and the laser transmitter.

The present invention further provides a mother glass inspection method, which comprises the following steps:

(1) providing a mother glass inspection device, wherein the mother glass inspection device comprises: a main body, a platform mounted on the main body, a light absorption layer formed on a top surface of the platform, a laser transmitter mounted on the main body and opposing the platform, and an image sensor arranged above the platform to correspond to the laser transmitter, the platform supporting a piece of mother glass to be laid flat thereon;

(2) providing a piece of mother glass to be inspected and placing the mother glass flat on the platform;

(3) activating the laser transmitter and also activating the image sensor to scan a surface of the mother glass, the laser transmitter transmitting a beam that is reflected by the mother glass toward the image sensor, a portion of the beam being refracted in the mother glass and absorbed by the light absorption layer;

(4) the image sensor transmitted an image message obtained through the inspection to the main body; and (5) the main body performing analysis according to the image message received to obtain an inspection result.

The light absorption layer is formed by coating a light absorption material on the platform.

The laser transmitter comprises a laser head and a reflector arranged to correspond to the laser head. The reflector reflects and re-directs a beam emitting from the laser head to the platform.

The image sensor comprises a photo detector. The photo detector is electrically connected to the main body to receive light emitting from the laser head and reflected by the mother glass.

The main body comprises: an enclosure and a circuit arrangement provided inside the enclosure. The circuit arrangement comprises a power module and a processing module. The power module is electrically connected to the processing module, the image sensor, and the laser transmitter. The processing module is further electrically connected to the image sensor and the laser transmitter.

The efficacy of the present invention is that the present invention provides a mother glass inspection device, which adopts a flat-laying type platform to support a piece of mother glass and provides a light absorption layer on the platform so as to eliminate fault inspection result of the image sensor caused by light reflection by stains present on the back side of the mother glass so that precisely identification if abnormality is present on a product can be made to prevent erroneous reworking or disposal thereby improving manufacturing efficiency and yield rate, shortening working hours, and lowering manufacturing cost. The mother glass inspection method according to the present invention is easily operated and may avoid fault result of inspection so as to prevent erroneous reworking or disposal for improving manufacturing efficiency and yield rate, shortening working hours, and lowering manufacturing cost.

For better understanding of the features and technical contents of the present invention, reference will be made to the following detailed description of the present invention and the attached drawings. However, the drawings are provided for the purposes of reference and illustration and are not intended to impose undue limitations to the present invention.

BRIEF DESCRIPTION OF THE DRAWINGS

The technical solution, as well as beneficial advantages, of the present invention will be apparent from the following detailed description of an embodiment of the present invention, with reference to the attached drawings. In the drawings.

DETAILED DESCRIPTION OF THE PREFERRED EMBODIMENTS

To further expound the technical solution adopted in the present invention and the advantages thereof, a detailed description is given to a preferred embodiment of the present invention and the attached drawings.

Figure 1:
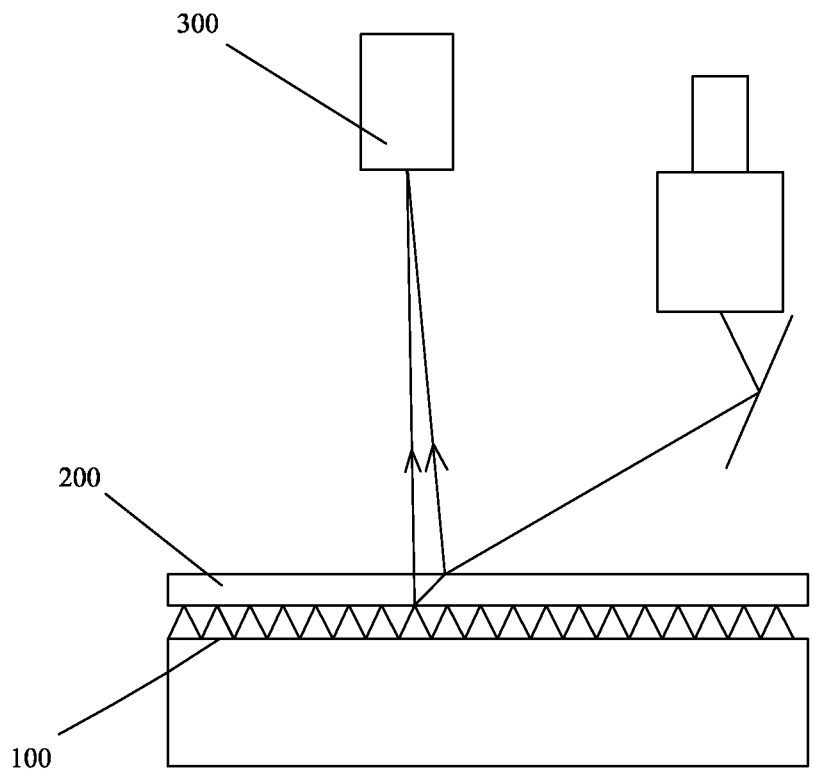
FIG. 1 is a schematic view showing a conventional mother glass inspection device.
Figure 2:
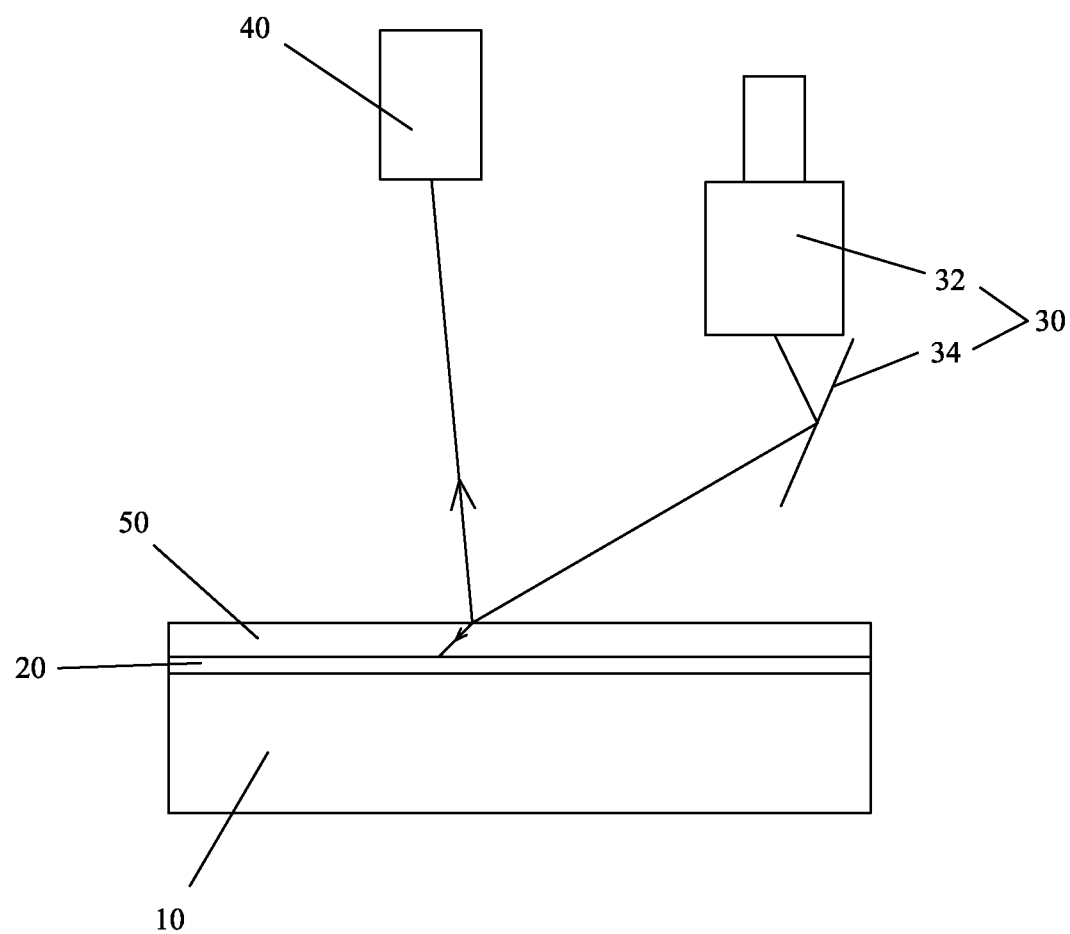
FIG. 2 is a schematic view showing a mother glass inspection device according to the present invention.

Referring to FIG. 2, the present invention provides a mother glass inspection device, which comprises: a main body (not shown), a platform 10 mounted on the main body, a light absorption layer 20 formed on a top surface of the platform 10, a laser transmitter 30 mounted on the main body and opposing the platform 10, and an image sensor 40 (which can be a CCD) arranged above the platform 10 to correspond to the laser transmitter 30. The platform 10 supports a piece of mother glass 50 to be laid flat thereon. The main body provides functions of general inspection of ordinary mother glass inspection devices. The mother glass 50 to be inspected is laid flat on the platform 10 and the laser transmitter 30 is activated to transmit a laser beam. The main body activates the image sensor 40 to scan a surface of the mother glass 50 in such a way that the laser beam reflected by the mother glass 50 is directed toward the image sensor 40 so that the image sensor 40 acquires an image message that is then transmitted to the main body to be analyzed by the main body for obtaining the inspection result. When a particle is present on the surface of the mother glass 50, the image sensor 40 receives a corresponding intensified signal, by which a determination is made for existence of the particle on the surface of the mother glass 50. With the mother glass inspection device, the influence on the result of inspection caused by a stain on a back of the mother glass 50 can be improved and fault result of inspection can be eliminated so that precisely identification if abnormality is present on a product can be made to prevent erroneous reworking or disposal thereby improving manufacturing efficiency and yield rate, shortening working hours, and lowering manufacturing cost.

The light absorption layer 20 functions to absorb light transmitting through the mother glass 50 so as to prevent the light from being reflected to cause fault inspection result of the image sensor 40. The light absorption layer 20 is formed by coating a light-absorbing material on the platform 10 and is alternatively formed by attaching a light absorption film to the platform 10.

The laser transmitter 30 comprises a laser head 32 and a reflector 34 arranged to correspond to the laser head 32. The laser head 32 emits the laser beam, which is reflected and re-directed by the reflector 34 to the surface of the mother glass 50. A portion of the beam is reflected and received by the image sensor 40, while a remaining portion of the beam is refracted toward the light absorption layer 20 and absorbed by the light absorption layer 20. The image sensor 40 comprises a photo detector (not labeled). The photo detector is electrically connected to the main body to detect and sample the light reflected from the mother glass 50 so as to determine if a particle is present o the surface of the mother glass by means of the light.

The main body comprises an enclosure and a circuit arrangement (not shown) provided inside the enclosure. The circuit arrangement comprises a power module and a processing module. The power module is electrically connected to the processing module, the image sensor 40, and the laser transmitter 30 to supply electrical power thereto. The processing module is further electrically connected to the image sensor 40 and the laser transmitter 30 to control activation/de-activation of the laser transmitter 30, analyze the image message transmitted from the image sensor 40, and thus obtain an inspection result of the mother glass. The inspection result comprises "pass" or "reject". In case of rejection, further analysis is made regarding number, size, and location of the particles.

Figure 3:
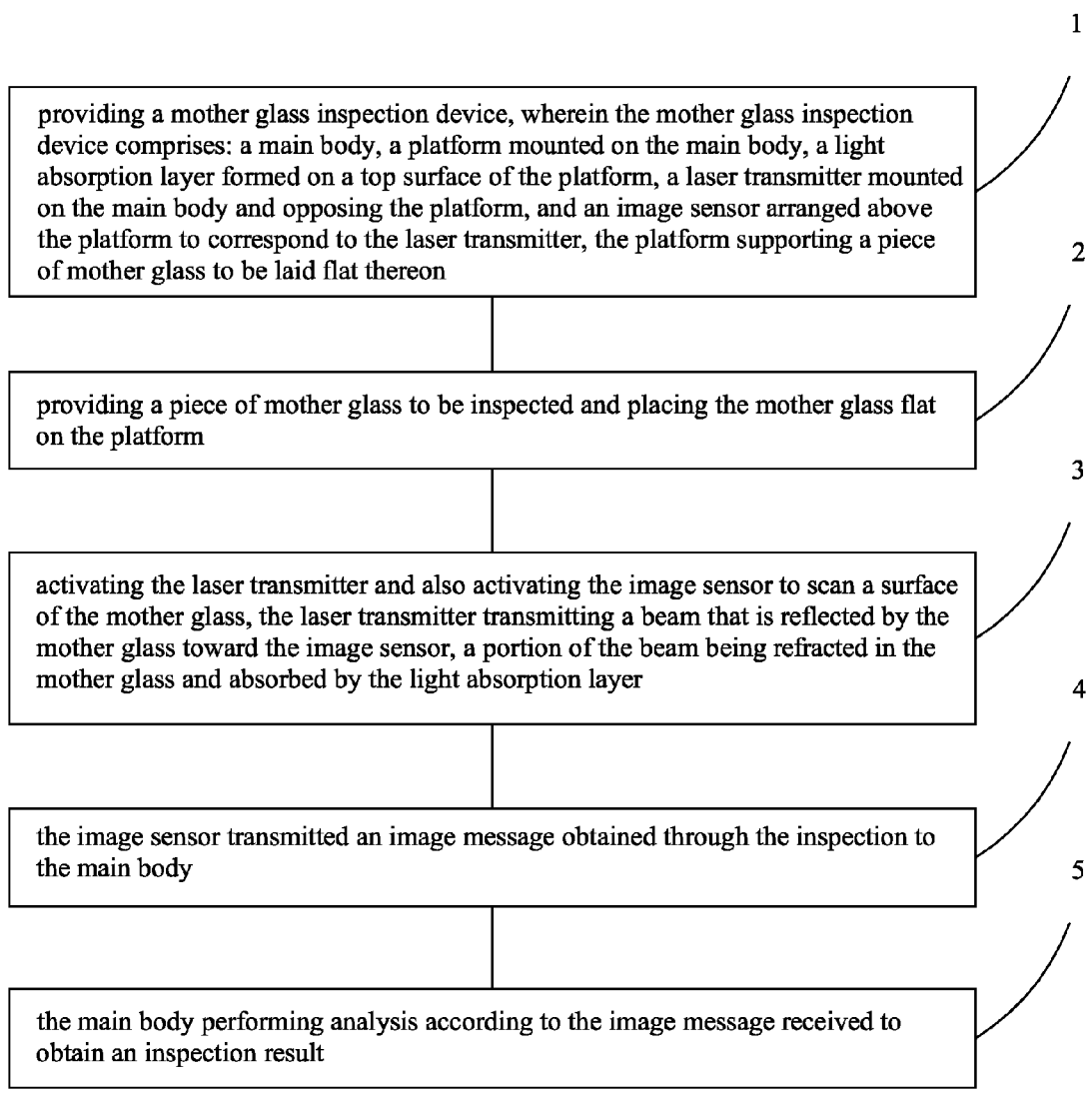
FIG. 3 is a flow chart illustrating a mother glass inspection method according to the present invention.

Referring to FIGS. 2 and 3, the present invention also provides a mother glass inspection method, which comprises the following steps:

Step 1: providing a mother glass inspection device, wherein the mother glass inspection device comprises: a main body (not shown), a platform 10 mounted on the main body, a light absorption layer 20 formed on a top surface of the platform 10, a laser transmitter 30 mounted on the main body and opposing the platform 10, and an image sensor 40 arranged above the platform 10 to correspond to the laser transmitter 30, the platform 10 supporting a piece of mother glass 50 to be laid flat thereon.

The light absorption layer 20 functions to absorb light transmitting through the mother glass 50 so as to prevent the light from being reflected to cause fault inspection result of the image sensor 40. The light absorption layer 20 is formed by coating a light-absorbing material on the platform 10 and is alternatively formed by attaching a light absorption film to the platform 10.

The laser transmitter 30 comprises a laser head 32 and a reflector 34 arranged to correspond to the laser head 32. The laser head 32 emits the laser beam, which is reflected and re-directed by the reflector 34 to the surface of the mother glass 50. A portion of the beam is reflected and received by the image sensor 40, while a remaining portion of the beam is refracted toward the light absorption layer 20 and absorbed by the light absorption layer 20. The image sensor 40 comprises a photo detector (not labeled). The photo detector is electrically connected to the main body to detect and sample the light reflected from the mother glass 50 so as to determine if a particle is present o the surface of the mother glass by means of the light.

The main body comprises an enclosure and a circuit arrangement (not shown) provided inside the enclosure. The circuit arrangement comprises a power module and a processing module. The power module is electrically connected to the processing module, the image sensor 40, and the laser transmitter 30 to supply electrical power thereto. The processing module is further electrically connected to the image sensor 40 and the laser transmitter 30 to control activation/de-activation of the laser transmitter 30, analyze the image message transmitted from the image sensor 40, and thus obtain an inspection result of the mother glass.

Step 2: providing a piece of mother glass 50 to be inspected and placing the mother glass 50 flat on the platform 10.

Step 3: activating the laser transmitter 30 and also activating the image sensor 40 to scan a surface of the mother glass 50, the laser transmitter 30 transmitting a beam that is reflected by the mother glass 50 toward the image sensor 40, a portion of the beam being refracted in the mother glass 50 and absorbed by the light absorption layer 20.

The laser head 32 is activated to transmit a laser beam and the photo detector is activated to scan the surface of the mother glass 50. The photo detector receives the light reflected from the mother glass 50.

Step 4: the image sensor 40 transmitted an image message obtained through the inspection to the main body.

In this Step, the image sensor 40 obtains the image message associated with the surface of the mother glass 50 according to the light reflected by the mother glass 50.

Step 5: the main body performing analysis according to the image message received to obtain an inspection result.

When a particle is present on the surface of the mother glass 50, the image sensor 40 receives a corresponding intensified signal, by which a determination is made for existence of the particle on the surface of the mother glass 50. The inspection result includes "pass" or "reject". In case of rejection, further analysis is made regarding number, size, and location of the particles.

In summary, the present invention provides a mother glass inspection device, which adopts a flat-laying type platform to support a piece of mother glass and provides a light absorption layer on the platform so as to eliminate fault inspection result of the image sensor caused by light reflection by stains present on the back side of the mother glass so that precisely identification if abnormality is present on a product can be made to prevent erroneous reworking or disposal thereby improving manufacturing efficiency and yield rate, shortening working hours, and lowering manufacturing cost. The mother glass inspection method according to the present invention is easily operated and may avoid fault result of inspection so as to prevent erroneous reworking or disposal for improving manufacturing efficiency and yield rate, shortening working hours, and lowering manufacturing cost.

Based on the description given above, those having ordinary skills of the art may easily contemplate various changes and modifications of the technical solution and technical ideas of the present invention and all these changes and modifications are considered within the protection scope of right for the present invention.

What is claimed is:

1. A mother glass inspection device, comprising: a main body, a platform, a light absorption layer arranged on a top surface of the platform, a laser transmitter mounted on the main body and opposing the platform, and an image sensor arranged above the platform to correspond to the laser transmitter, the platform being adapted to support a piece of mother glass to be laid flat thereon, wherein an intensified signal is generated when a particle is detected on a surface of the mother glass and wherein the light absorption layer is formed of a light absorption film attached to the platform to support a back of the mother glass thereon and to be opposite to the image sensor with respect to the mother glass and eliminate reflection of light by the back of the mother glass to interfere with the intensified signal detected by the image sensor.

2. The mother glass inspection device as claimed in claim 1, wherein the laser transmitter comprises a laser head and a reflector arranged to correspond to the laser head, the reflector reflecting and re-directing a beam emitting from the laser head to the platform.

3. The mother glass inspection device as claimed in claim 2, wherein the image sensor comprises a photo detector, the photo detector being electrically connected to the main body to receive light emitting from the laser head and reflected by the mother glass.

4. A mother glass inspection device, comprising: a main body, a platform, a light absorption layer arranged on a top surface of the platform, a laser transmitter mounted on the main body and opposing the platform, and an image sensor arranged above the platform to correspond to the laser transmitter, the platform being adapted to support a piece of mother glass to be laid flat thereon, wherein an intensified signal is generated when a particle is detected on a surface of the mother glass;

wherein the light absorption layer is formed of a light absorption film attached the platform to support a back of the mother glass thereon and to be opposite to the image sensor with respect to the mother glass and eliminate reflection of light by the back of the mother glass to interfere with the intensified signal detected by the image sensor;

wherein the laser transmitter comprises a laser head and a reflector arranged to correspond to the laser head, the reflector reflecting and re-directing a beam emitting from the laser head to the platform; and wherein the image sensor comprises a photo detector, the photo detector being electrically connected to the main body to receive light emitting from the laser head and reflected by the mother glass.

5. A mother glass inspection method, comprising the following steps:

(1) providing a mother glass inspection device, wherein the mother glass inspection device comprises: a main body, a platform, a light absorption layer arranged on a top surface of the platform, a laser transmitter mounted on the main body and opposing the platform, and an image sensor arranged above the platform to correspond to the laser transmitter, the platform supporting a piece of mother glass to be laid flat thereon;

(2) providing a piece of mother glass to be inspected and placing the mother glass flat on the platform;

(3) activating the laser transmitter and also activating the image sensor to scan a surface of the mother glass, the laser transmitter transmitting a beam that is reflected by the mother glass toward the image sensor, a portion of the beam being refracted in the mother glass and absorbed by the light absorption layer;

(4) the image sensor transmitted an image message obtained through the inspection to the main body; and (5) the main body performing analysis according to the image message received to obtain an inspection result;

wherein an intensified signal is generated when a particle is detected on a surface of the mother glass and wherein the light absorption layer is formed of a light absorption film attached to the platform to support a back of the mother glass thereon and to be opposite to the image sensor with respect to the mother glass and absorb the refracted portion of the light and eliminate reflection of the refracted portion of the light by the back of the mother glass to interfere with the intensified signal detected by the image sensor.

6. The mother glass inspection method as claimed in claim 5, wherein the laser transmitter comprises a laser head and a reflector arranged to correspond to the laser head, the reflector reflecting and re-directing a beam emitting from the laser head to the platform.

7. The mother glass inspection method as claimed in claim 6, wherein the image sensor comprises a photo detector, the photo detector being electrically connected to the main body to receive light emitting from the laser head and reflected by the mother glass.

* * * * *